United States Patent
Moon et al.

(10) Patent No.: US 10,070,834 B2
(45) Date of Patent: Sep. 11, 2018

(54) X-RAY PHOTOGRAPHY DEVICE CAPABLE OF PHOTOGRAPHING IN VARIOUS PHOTOGRAPHY MODES

(71) Applicant: LISTEM CORPORATION, Wonju-si, Gwangwon-do (KR)

(72) Inventors: Chang Ho Moon, Seoul (KR); Jung Hyun Moon, Wonju-si (KR); Sang Jin Moon, Seoul (KR); Jung Wook Shin, Wonju-si (KR)

(73) Assignee: Listem Corporation, Wonju-si Gangwon- (KR)

( * ) Notice: Subject to any disclaimer, the term of this patent is extended or adjusted under 35 U.S.C. 154(b) by 247 days.

(21) Appl. No.: 14/785,612

(22) PCT Filed: Mar. 31, 2014

(86) PCT No.: PCT/KR2014/002738
§ 371 (c)(1),
(2) Date: Oct. 19, 2015

(87) PCT Pub. No.: WO2014/171647
PCT Pub. Date: Oct. 23, 2014

(65) Prior Publication Data
US 2016/0073985 A1 Mar. 17, 2016

(30) Foreign Application Priority Data

Apr. 19, 2013 (KR) .................. 10-2013-0043309
Mar. 13, 2014 (KR) .................. 10-2014-0029890

(51) Int. Cl.
*H01J 31/49* (2006.01)
*A61B 6/00* (2006.01)

(52) U.S. Cl.
CPC ............ *A61B 6/4429* (2013.01); *A61B 6/447* (2013.01)

(58) Field of Classification Search
CPC .............................. A61B 6/4429; A61B 6/447
(Continued)

(56) References Cited

U.S. PATENT DOCUMENTS 4,484,343 A * 11/1984 Cesar .................. A61B 6/0457
378/196
6,152,598 A * 11/2000 Tomisaki ............. A61B 6/0457
378/188
(Continued)

FOREIGN PATENT DOCUMENTS

JP         10-127624 A      5/1998
JP        2006-255090 A     9/2006
(Continued)

OTHER PUBLICATIONS

International Search Report dated Jul. 7, 2014 of PCT/KR2014/002738 which is the parent application and its English translation—4 pages.

*Primary Examiner* — Courtney Thomas
(74) *Attorney, Agent, or Firm* — Knobbe Martens Olson & Bear LLP; Mincheol Kim

(57) ABSTRACT

An X-ray photography device capable of readily photographing by switching to various photography modes such as a standing mode, a table mode and the like with one X-ray photography device is disclosed. To this end, the X-ray photographing device comprises: a base frame; a support frame pivotably coupled to one side of the base frame through a hinge shaft and on one side of which an X-ray detector for detecting X-rays irradiated from an X-ray generation device is slidably provided; and an actuator of which one end is rotatably fixed to the base frame and of which the other end is rotatably fixed to the support frame spaced at a predetermined distance from the hinge shaft, and which pivots the support frame around the hinge shaft within a predetermined angle range while moving a driving shaft (Continued)

therein forward and backward by pneumatic or hydraulic pressure supplied from the outside.

16 Claims, 15 Drawing Sheets

(58) Field of Classification Search
USPC .................................................. 378/193–197
See application file for complete search history.

(56) References Cited

U.S. PATENT DOCUMENTS

| | | | |
|---|---|---|---|
| 6,851,851 B2* | 2/2005 | Smith | A61B 6/0457 378/167 |
| 2010/0232574 A1* | 9/2010 | Ahn | A61B 6/447 378/167 |

FOREIGN PATENT DOCUMENTS

| | | |
|---|---|---|
| KR | 10-0484613 B1 | 4/2005 |
| KR | 10-2012-0115692 A | 10/2012 |
| KR | 10-2013-0005905 A | 1/2013 |

* cited by examiner

X-RAY PHOTOGRAPHY DEVICE CAPABLE OF PHOTOGRAPHING IN VARIOUS PHOTOGRAPHY MODES

TECHNICAL FIELD

The present invention relates to an X-ray imaging apparatus capable of easily performing imaging by switching a mode to various imaging modes such as a standing mode and a table mode using one X-ray imaging apparatus.

BACKGROUND ART

In general, X-ray imaging apparatuses are medical apparatuses that are used for radiographic examinations using images of internal diseases of human bodies, and analyze whether a bone of human bodies is damaged in a chest, a head, gastrointestinal tracts, vertebrae and injured areas of human bodies through X-rays.

In general, such X-ray imaging apparatuses have different imaging modes, a standing mode in which imaging is performed while a patient stands up and a table mode in which imaging is performed while the patient is lying on a table. Here, when imaging is performed in the standing mode, imaging is performed while an X-ray detector mounted to be vertically movable on a wall surface or a post positioned at a side opposite to an X-ray generator is gripped with a hand, and the X-ray detector is raised or lowered to an appropriate height according to a required imaging area. When imaging is performed in the table mode, while the X-ray detector is disposed at a lower end of the table, the X-ray generator installed at a ceiling opposite thereto is moved up, down, left or right and disposed at an appropriate position, and then imaging is performed.

In Korean Patent No. 10-0484613, an example of a stand type X-ray imaging apparatus in which X-ray imaging can be performed while the patient stands up is disclosed. As illustrated in FIG. 1, the X-ray imaging apparatus disclosed in the above patent includes a vertical frame 2 including a support or a plate, a driving motor 6 disposed at one side of the vertical frame 2 and having a different voltage output, a driving wheel 8 that is disposed above the vertical frame 2 and connected to the driving motor 6, a wire 10 to be wound on the driving wheel 8, a weight 12 installed to be suspended from one end of the wire 10, an X-ray detector 16 that is connected to the other end of the wire 10 and slidably moves along the vertical frame 2, an automatic manipulation switch 18 configured to rotate the driving motor 6 forward or backward, and a gripping unit 22 configured to manually push or pull the X-ray detector 16. The X-ray imaging apparatus having such a configuration images a body area of the patient when an operator grips the gripping unit 22 of the X-ray detector 16 while X-ray imaging is performed, moves up or down the X-ray detector 16 to be positioned at an appropriate imaging area, and then emits X-rays from an X-ray generator (not illustrated) positioned at a side opposite to the X-ray detector 16 to the X-ray detector.

However, the above-described stand type X-ray imaging apparatus of the related art was designed such that X-ray imaging is possible only when the patient stands up. Therefore, in order to perform imaging while the patient is lying on the table, a separate X-ray imaging device dedicated for the table mode is necessary. In this manner, general X-ray imaging apparatuses of the related art were designed to be used only in the standing mode or the table mode. Therefore, there are problems in that a separate X-ray imaging apparatus dedicated for each imaging mode is necessary, and accordingly an installation cost excessively increases due to redundant installations of expensive X-ray imaging apparatuses, or an installation space is not efficiently utilized.

DISCLOSURE

Technical Problem

In view of the above-described problems, the present invention provides an X-ray imaging apparatus configured such that, in a stand type X-ray imaging apparatus of the related art, a support frame supporting an X-ray detector is pivotally fixed to one side of a base frame fixed to an installation bottom surface, an actuator installed at the base frame is driven, and the support frame is pivotable at a predetermined angle. Therefore, an imaging task can be performed in various imaging modes such as a standing mode and a table mode using one X-ray detecting device. It is possible to minimize an installation cost according to additional installation of an X-ray imaging apparatus for each imaging mode and efficiently utilize an installation space, unlike the related art.

The present invention also provides an X-ray imaging apparatus in which manual manipulation of an X-ray detector is easily performed through a balancing weight when the X-ray detector is gripped with a hand and a position adjusting task is manually performed, and it is possible to prevent damage of a device and safety problems caused when a wire wound on a wheel inside an X-ray detecting device is separated from the wheel in a process in which a mode of the X-ray detecting device is switched from a standing imaging mode to a table imaging mode or switched reversely.

The present invention also provides an X-ray imaging apparatus in which an X-ray detecting device and a table are implemented as one set in a certain area in an assembling manner, and thus it is possible to perform imaging by freely changing a mode of the X-ray imaging apparatus to a standing mode or a table mode even in a narrow space, that is, a limited installation space.

Technical Solution

In view of the above-described problems, an X-ray imaging apparatus according to the present invention includes a base frame; a support frame pivotally combined with one side of the base frame and having one side at which an X-ray detector configured to detect X-rays emitted from an X-ray generating device is slidably installed; and an actuator including one end that is pivotally fixed to the base frame and the other end that is pivotally fixed to the support frame, and enabling the support frame to be pivoted in a predetermined angle range.

Here, the present invention may further include a first wheel rotatably fixed to one inner end of the support frame; a second wheel rotatably fixed to the other inner end of the support frame facing the first wheel; a wire that is connected to the first wheel and the second wheel and forms a closed loop shape; and a balancing weight configured to maintain a balance with the X-ray detector.

In this case, the wire may include a first wire including one end that is fixed to the X-ray detector and the other end that is fixed to the balancing weight while being wound on the first wheel; and a second wire including one end that is fixed to the X-ray detector and the other end that is fixed to the balancing weight while being wound on the second wheel.

Also, the present invention may further include a driving motor installed at the support frame and configured to transmit rotary power to either the first wheel or the second wheel; and a manipulation switch configured to manipulate the driving motor to be rotatably driven forward or backward.

Also, the X-ray detector may include a detector body having a plate shape; and a sliding frame that is combined with a rear side of the body and slidably moves in a lengthwise direction of the support frame, wherein ends of the first wire and the second wire may be detachably connected through a fixing bracket fixed to the sliding frame.

In addition, both ends of the first wire and both ends of the second wire may be detachably combined with the fixing bracket of the sliding frame and the balancing weight through wire fixing screws.

Meanwhile, in view of the above-described problems, an X-ray imaging apparatus according to another aspect of the present invention includes a base frame installed to be slidably linearly movable on a bottom portion; a support frame pivotally combined with one side of the base frame and having one side at which an X-ray detector configured to detect X-rays emitted from an X-ray generating device is slidably installed; an actuator including one end that is pivotally fixed to the base frame and the other end that is pivotally fixed to the support frame, and enabling the support frame to be pivoted in a predetermined angle range; a driving unit configured to drive such that the base frame slidably linearly moves on the bottom portion; a table installed above the bottom portion in a tiltable manner; a tilting unit configured to tilt the table; and a control unit configured to control the actuator, the driving unit, and the tilting unit.

Here, the control unit may control the driving unit and the actuator such that a sliding linear movement of the base frame and a rotational movement of the support frame with respect to the base frame are able to be performed simultaneously.

The control unit may be a foot switch that is attached to the bottom portion and is manipulated by a foot.

The table may include an upper plate; a pair of fixed leg portions whose lower end is fixed to the bottom portion and whose upper end is rotatably combined with the upper plate by a hinge; and a pair of rotating leg portions that are positioned at a side opposite to the upper plate facing the fixed leg portion and have an upper end that is rotatably combined with the upper plate by a hinge and a lower end that is mounted on the bottom portion.

Here, a parking device configured to park the rotating leg portion to be mounted at a normal position may be installed in a part of the bottom portion on which the rotating leg portion is mounted.

In this case, the parking device may be installed into a groove formed at both corner parts of the bottom portion.

The parking device may include a leg pedestal portion made of a shock-absorbing material attached to a lower end of the rotating leg portion; a U-shaped mounting unit on which the leg pedestal portion is inserted and mounted; and a leading unit configured to lead the leg pedestal portion to be inserted into the mounting unit.

Meanwhile, the tilting unit may include a first bracket combined with a fixed leg portion; a second bracket combined with an upper plate; and a cylinder that includes a lower end combined with the first bracket by a hinge and an upper end combined with the second bracket by a hinge, and tilts up and down the upper plate.

In this case, the cylinder may be an electric cylinder that rotates a motor inside the cylinder forward or backward when power is applied and reciprocates a rod.

Also, the tilting unit may be installed at at least one of a pair of fixed leg portions.

Also, the driving unit may include a driving motor installed inside the base frame; a plurality of casters that are rotatably installed at a lower end of the base frame and move along an upper surface of the bottom portion in a rolling manner; a power transmission device connecting the driving motor and the caster and configured to transmit power of the driving motor to the caster; and a guide unit configured to guide the caster to be moved along a determined linear trajectory.

Advantageous Effects

The present invention having the above configuration is configured such that, in the stand type X-ray detecting device, the support frame supporting the X-ray detector is pivotally combined with one side of the base frame through a hinge shaft, the actuator is installed between the base frame and the support frame, and the support frame is freely pivotable about the hinge shaft in a predetermined angle range through the actuator. Therefore, imaging can be performed using one X-ray detecting device by switching a mode to various imaging modes such as the standing mode and the table mode. In addition, unlike the related art, since there is no need to separately provide a dedicated imaging apparatus for performing imaging in the standing mode or the table mode, it is possible to reduce an installation cost. Since a separate dedicated installation space for each imaging mode is unnecessary, it is possible to maximize an installation space utilization.

Also, a wire connection structure having a closed loop shape in which the first wheel and the second wheel are rotatably fixed to both inner ends of the support frame of the X-ray detecting device and the wire is wound on and connects the first wheel and the second wheel is formed. Therefore, when a mode of the X-ray detecting device is switched from the standing imaging mode to the table imaging mode or switched reversely, it is possible to prevent the wire wound on two wheels from being released and separated from the wheel. Accordingly, it is possible to prevent component damage and safety problems caused when the wire is separated from the wheel and thus the balancing weight is separated.

Also, both ends of the first wire wound on the first wheel and the second wire wound on the second wheel are detachably combined with the fixing bracket of the sliding frame and the balancing weight through a separate wire fixing screw. Therefore, since wire fixing screws fixed to both ends of the first and second wires can be easily separated from and recombined with the fixing bracket of the sliding frame or the balancing weight as necessary, it is possible to easily replace or repair a component when an internal component is damaged.

Also, the X-ray detector is installed to be horizontally movable in a front and rear direction of the bottom plate, and simultaneously the table is installed to be tiltable in a vertical direction. Therefore, when imaging is performed in the standing mode, the imaging task can be performed while the table is tilted up and then the X-ray detecting device is horizontally moved in one direction and is in an upright state. When imaging is performed in the table mode, the upright X-ray detecting device is slidably moved in an opposite direction again and is placed in a horizontal state, the table is tilted down again to be restored to an original state, and thus the imaging task can be performed in the table mode. Therefore, even in a narrow space, that is, a limited space, it is possible to easily perform the X-ray imaging task by freely changing a mode to the standing mode or the table mode using the X-ray imaging apparatus of the present invention. It is possible to suppress an additional increase in costs necessary for ensuring an installation space according to separate installation of the X-ray detecting device and the table in different spaces.

Also, when the control unit controls such that a sliding linear movement of the base frame and a rotational movement of the support frame with respect to the base frame are simultaneously performed, it is possible to reduce the number of control units for separately controlling the linear movement of the base frame and the rotational movement of the support frame. When the control unit sequentially separately operates configuration units, it is possible to address possible inconvenience in use and a time delay problem. In addition, when the foot switch is installed at a bottom portion as the control unit, since the user can easily manipulate the foot switch provided at the bottom portion with his or her foot, it is possible to increase convenience in use.

Also, a separate parking device is installed at the bottom portion on which a rotating leg portion of the table is mounted. Therefore, when the table is tilted down, the rotating leg portion is guided to a determined position and easily mounted through the parking device. While the rotating leg portion is mounted in the parking device, it can be firmly fixed without an unbalanced sliding motion.

EMBODIMENTS

Hereinafter, embodiments of the present invention will be described in detail with reference to the accompanying drawings.

Figure 1:
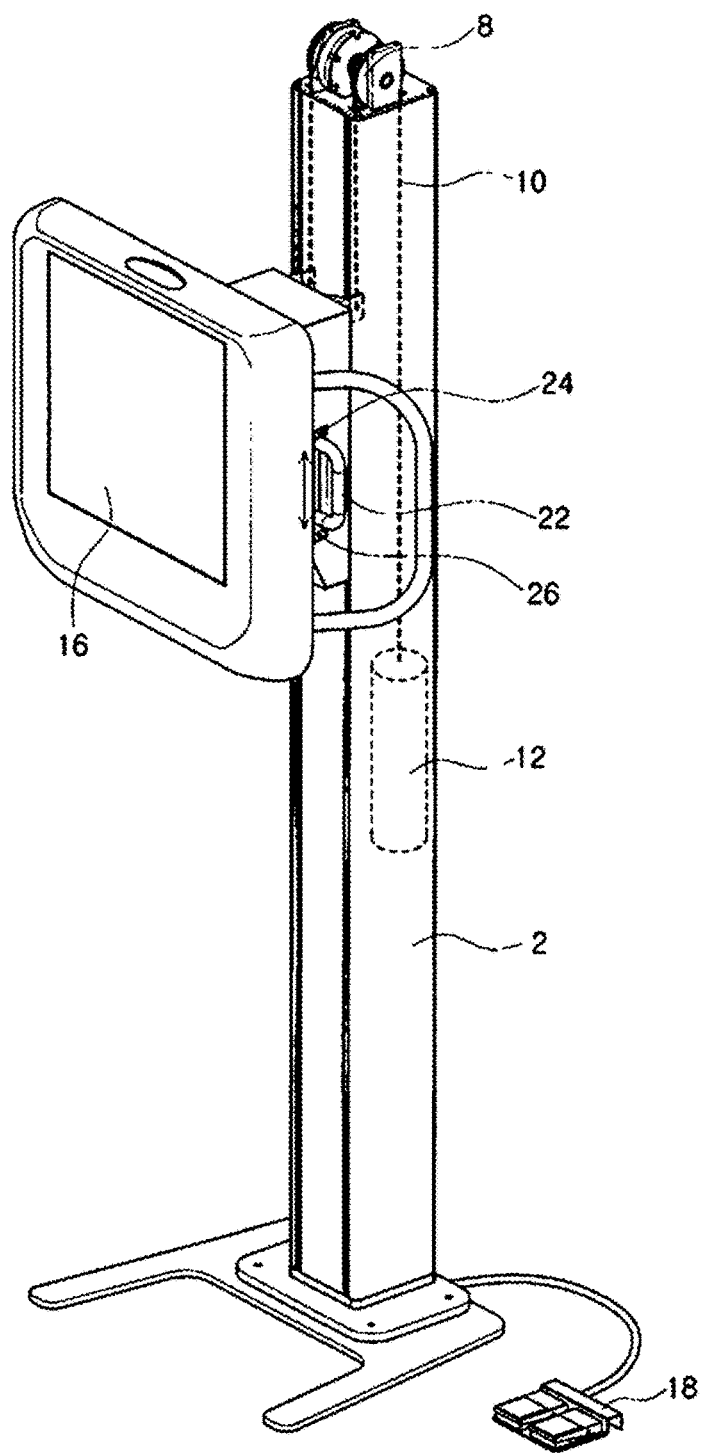
FIG. 1 is a perspective view of an X-ray imaging apparatus according to the related art.
Figure 2:
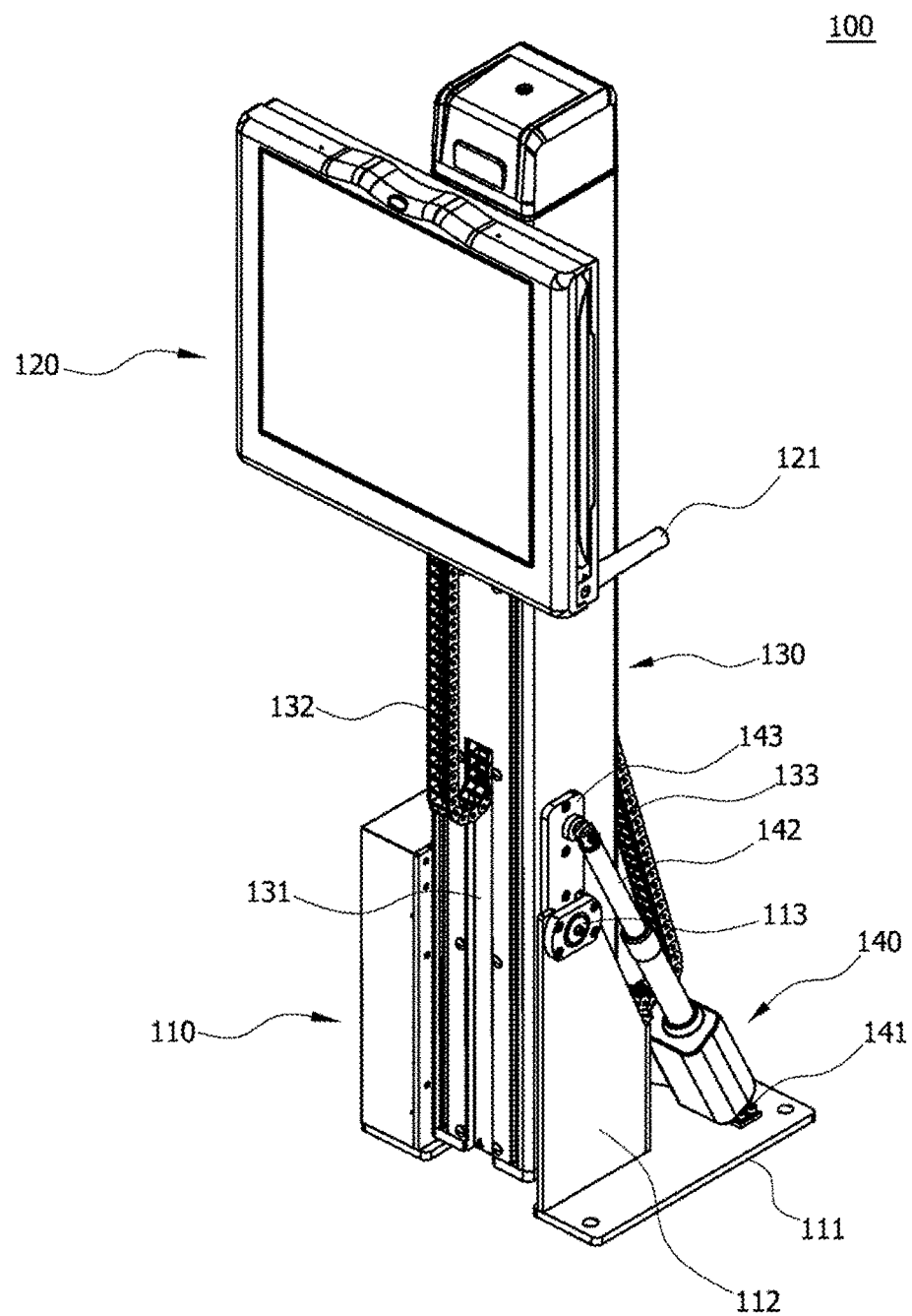
FIG. 2 is a perspective view of an X-ray imaging apparatus according to an embodiment of the present invention.
Figure 3:
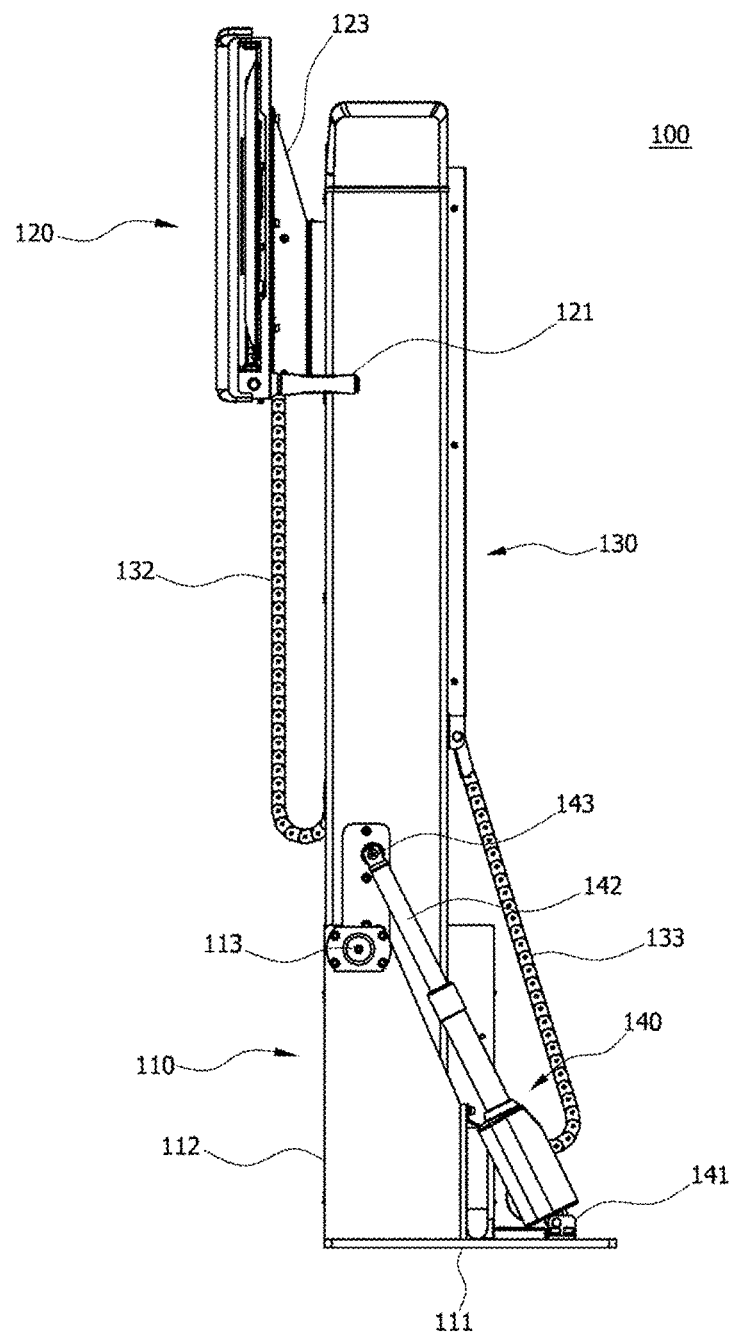
FIG. 3 is a side view of FIG. 2.

FIG. 2 is a perspective view of an X-ray detecting device configured to detect X-rays emitted from an X-ray generating device in an X-ray imaging apparatus according to an embodiment of the present invention. FIG. 3 is a side view seen from a side of FIG. 2.

As illustrated in FIGS. 2 and 3, the X-ray imaging apparatus according to the present invention includes an X-ray generating device configured to generate X-rays and an X-ray detecting device configured to detect X-rays emitted from the X-ray generating device.

Here, as illustrated in FIGS. 2 and 3, an X-ray detecting device 100 includes a base frame 110 fixed to a bottom surface of an installation target, a support frame 130 that is pivotally fixed to the base frame 110 and at which an X-ray detector 120 configured to detect X-rays is installed to be vertically movable, and an actuator 140 configured to pivot the support frame 130 at which the X-ray detector 120 is installed in a predetermined angle range with respect to the base frame 110.

The base frame 110 includes a horizontal portion 111 that is fixed to the bottom surface of the installation target and has a bracket shape, and a pair of vertical portions 112 that are separated at a certain interval such that a lower end of the support frame 130 can be inserted and vertically stand on to be fixed to the horizontal portion 111.

Also, the lower end of the support frame 130 is inserted between both of the vertical portions 112 of the base frame 110 and then is pivotally combined at the outside of the vertical portion 112 through a hinge shaft 113. Therefore, the support frame 130 remains in a state in which pivoting about an area with which the hinge shaft 113 is combined is possible with respect to the base frame 110 fixed to the bottom surface.

The X-ray detector 120 configured to detect X-rays emitted from an X-ray generator (not illustrated) is provided at an upper front side of the support frame 130. The X-ray detector 120 is combined with a front side part of a sliding frame 123 that is vertically slidably installed inside the support frame 130, and vertically moves in linkage with a vertical direction movement of the sliding frame 123. Also, a pair of handgrip portions 121 configured for a user to grip and manually vertically transfer the X-ray detector 120 with both hands are provided at a lower end of a rear surface portion of the X-ray detector 120.

The actuator 140 is a driving unit capable of pivoting the support frame 130 clockwise or counter-clockwise and has a lower end that is rotatably combined with a bracket 141 fixed to a side of the horizontal portion 111 of the base frame 110 and an upper end that is rotatably combined with a side surface of the support frame 130 separated a predetermined distance in an upper direction from the hinge shaft 113 through a bracket 143.

The actuator 140 advances and retreats a driving shaft (piston shaft) 142 provided therein according to a pneumatic pressure or a hydraulic pressure supplied from the outside, pivots the support frame 130 clockwise or counter-clockwise with respect to the hinge shaft 113, and regulates an angle of the support frame 130 in a certain angle range. In this case, supply of the pneumatic pressure or the hydraulic pressure supplied to the actuator 140 or an advancing and retreating direction of the driving shaft 142 of the actuator are selected according to an operation of a manipulation switch 180 provided at the outside.

Figure 6:
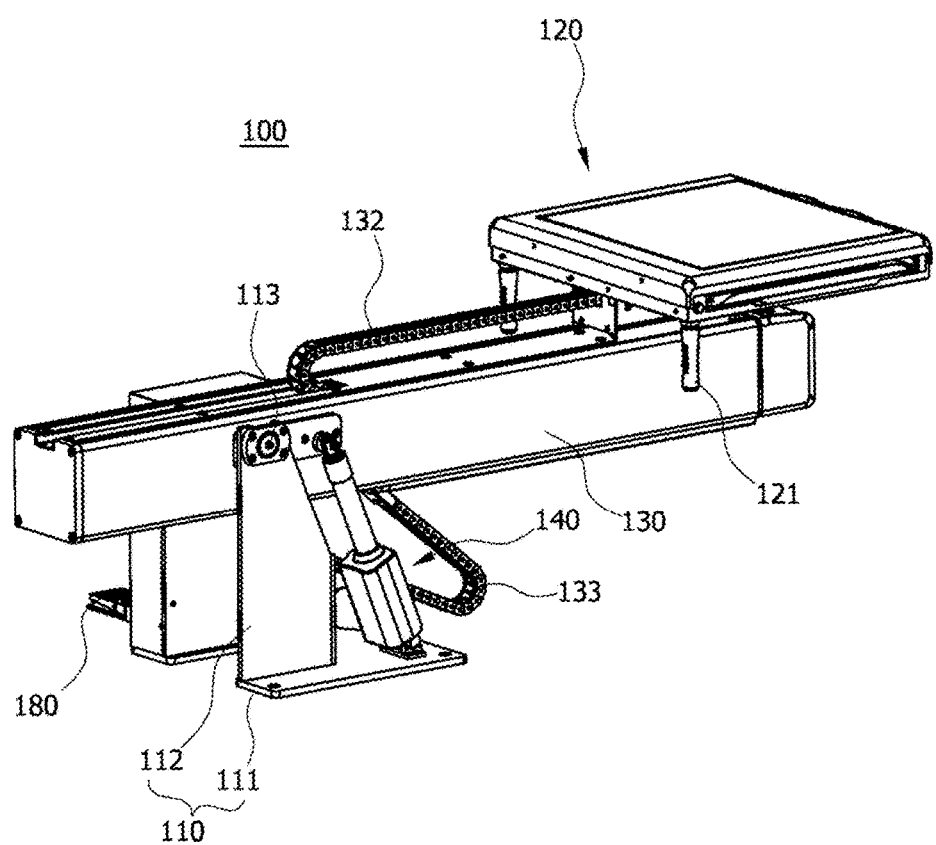
FIG. 6 is an operation state diagram illustrating a state in which a support frame of the X-ray imaging apparatus illustrated in FIG. 2 is rotated 90 degrees.

For example, while the driving shaft 142 is completely withdrawn from the actuator 140, as illustrated in FIG. 2, the support frame 130 on which the X-ray detector 120 is mounted remains in an upright state in which the support frame 130 vertically stands on the bottom surface, and X-ray imaging can be performed on a patient in a standing mode. On the other hand, while the driving shaft 142 is completely inserted into the actuator 140, as illustrated in FIG. 6, the support frame 130 remains in a horizontal state, that is, in parallel to the bottom surface, and X-ray imaging can be performed on the patient in a table mode.

In this manner, since the actuator 140 provided at the outside of the support frame 130 is driven to freely switch a state of the support frame 130 to a vertical or horizontal state, an X-ray imaging task can be performed using one X-ray detecting device 100 by easily changing a mode to the standing mode or the table mode. In addition, since a rotation angle of the support frame 130 by the actuator 140 can be variously changed in an angle range of 0 to 90 degrees, the X-ray imaging task can be performed on the patient in various several postures.

Reference numerals 132 and 133 (not described) denote a cable carrier in which various data cables, power cables for driving the X-ray detecting device 100 and the like are accommodated. Reference numeral 131 denotes a groove formed at the front of the support frame 130 to temporarily accommodate a part of the cable carrier when the X-ray detector 120 is raised or lowered.

Figure 4:
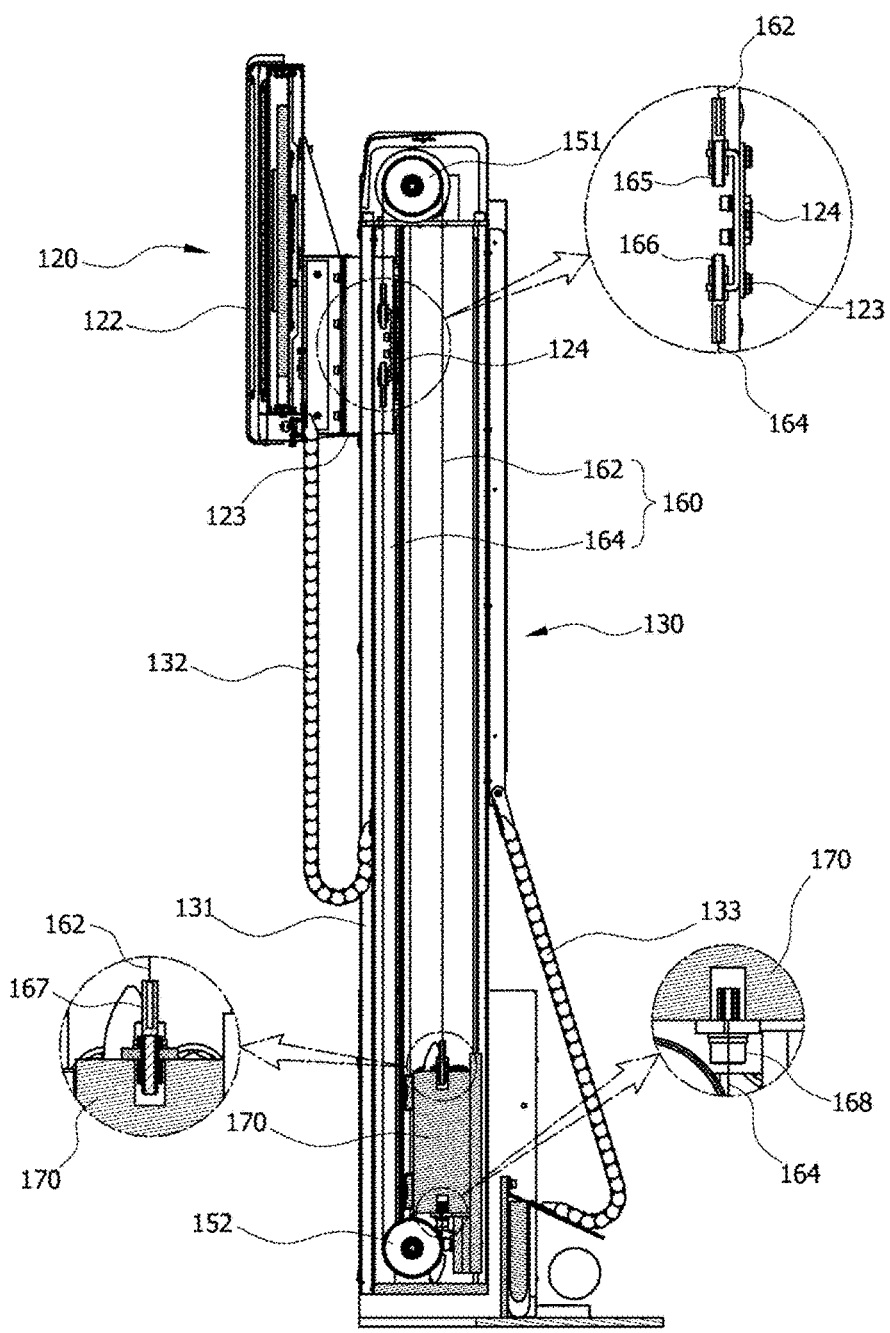
FIG. 4 is a cross-sectional view of FIG. 3.
Figure 5:
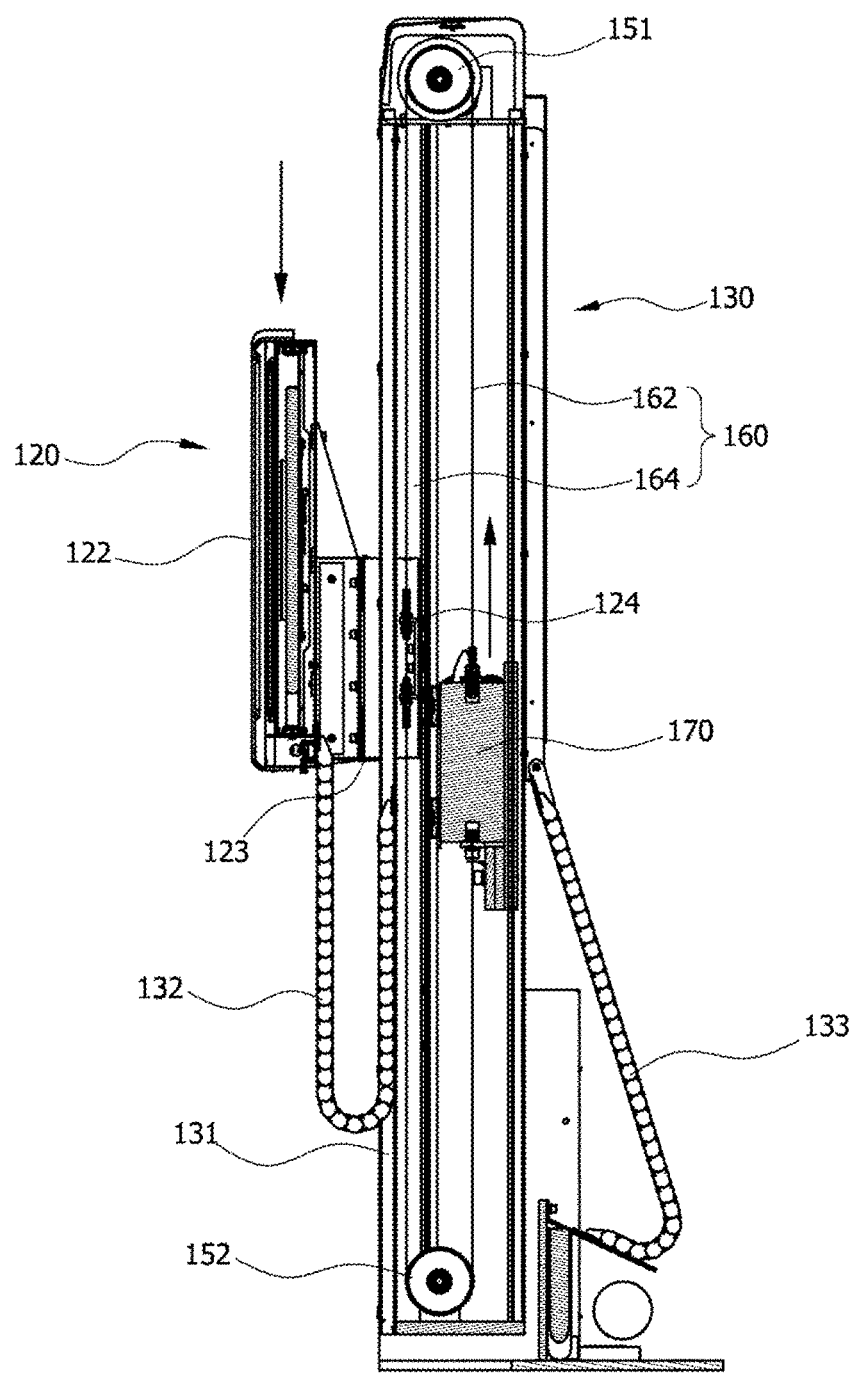
FIG. 5 is an operation state diagram illustrating a state in which an X-ray detector of FIG. 4 is lowered to a predetermined distance.

Meanwhile, FIG. 4 is a cross-sectional view illustrating a detailed internal structure of the X-ray detecting device 100 in the X-ray imaging apparatus according to the present invention. FIG. 5 is an operation state diagram illustrating a state in which the X-ray detector 120 of FIG. 4 is lowered to a certain distance along the support frame 130.

As illustrated in FIGS. 4 and 5, in the X-ray detecting device 100 according to the present invention, a first wheel 151 is rotatably fixed to an upper inner end of the support frame 130 and a second wheel 152 is rotatably fixed to a lower inner end of the support frame 130 facing the first wheel 151. Also, the first wheel 151 and the second wheel 152 on which a wire 160 is simultaneously wound are connected to each other, and form a wire connection structure having a closed loop shape as a whole. Also, a balancing weight 170 configured to maintain a balance when the X-ray detector 120 vertically slidably moves is installed on the wire 160 positioned at a side opposite to the X-ray detector 120.

The first wheel 151 is rotatably fixed to the upper inner end of the support frame 130, is connected to a driving motor (not illustrated) provided inside the support frame 130 through a power transmission member (for example, a belt), receives a rotary power of the driving motor through the power transmission member, and rotates forward or backward. Here, a forward or backward rotation operation of the driving motor is performed through the manipulation switch 180 provided at the outside of the X-ray detecting device 100. In this case, the manipulation switch 180 has a form of a foot switch that an operator who will perform the X-ray imaging task can step on for manipulation.

The second wheel 152 is rotatably fixed to the lower inner end of the support frame 130 positioned at a side opposite to the first wheel 151. Also, the first wheel 151 positioned at an upper side and the second wheel 152 positioned at a lower side are connected through the wire 160, and when the first wheel 151 rotates, the second wheel 152 also rotates in the same direction in linkage therewith. In addition, in the wire 160 wound between the first wheel 151 and the second wheel 152, parts of a front side and rear side thereof linearly move in opposite directions with respect to an imaginary center line connecting rotation axes of the first wheel 151 and the second wheel 152.

In this case, since the wire 160 has a connection structure in which the first wheel 151 and the second wheel 152 form a closed loop, the wire 160 serves as a power transmission member that transmits rotary power of the first wheel 151 to the second wheel 152. In addition, the second wheel 152 serves as a wire support unit enabling the wire 160 to remain in a linearly tight state together with the first wheel 151.

The X-ray detector 120 includes an X-ray detector body 122 having a plate shape and the sliding frame 123 that is combined with a rear side of the X-ray detector body 122 and slidably transfers in a vertical direction (a lengthwise direction) while being accommodated inside the support frame 130.

The balancing weight 170 is provided to have a weight similar to a total weight of the X-ray detector 120 such that a mutual weight balance with the X-ray detector 120 positioned at a front side opposite thereto can be maintained. The balancing weight 170 is connected to the X-ray detector 120 through the wire 160, and when the X-ray detector 120 is raised, is lowered, and otherwise when the X-ray detector 120 is lowered, is raised. Accordingly, a weight balance with the X-ray detector 120 is maintained. Therefore, when the operator vertically moves the X-ray detector 120 and manually performs a position adjusting task, the operator can easily and conveniently perform a vertical transfer task of the X-ray detector 120 effortlessly.

Meanwhile, the wire 160 has a structure in which two wires are connected to each other and includes a first wire 162 to be wound on a part of the first wheel 151 and a second wire 164 to be wound on a part of the second wheel 152.

Here, while the first wire 162 is wound on the first wheel 151 positioned at the upper inner end of the support frame 130, one end thereof is fixed to an upper end of the sliding frame 123 on which the X-ray detector 120 is mounted, and the other end thereof is fixed to an upper end of the balancing weight 170 positioned at a side opposite to the X-ray detector 120.

In this case, while one end of the first wire 162 fixed to the upper end of the sliding frame 123 is connected to a wire fixing screw 165, when the wire fixing screw 165 is fastened to an upper end of a fixing bracket 124 that is fixed to the sliding frame 123 and has a bracket shape, fixation is performed. In addition, when the other end of the first wire 162 is connected to a wire fixing screw 167 and then is fastened to the upper end of the balancing weight 170 positioned at a side opposite thereto through the wire fixing screw 167, fixation is performed.

While the second wire 164 is wound on the second wheel 152 positioned at the lower inner end of the support frame, one end thereof is fixed to a lower end of the sliding frame 123 and the other end thereof is fixed to a lower end of the balancing weight 170.

In this case, while one end of the second wire 164 fixed to the lower end of the sliding frame 123 is connected to a wire fixing screw 166, when the wire fixing screw 166 is fastened to a lower end of the fixing bracket 124 fixed to the sliding frame 123, fixation is performed. In addition, while the other end of the second wire 164 is connected to a wire fixing screw 168, when the wire fixing screw 168 is fastened to a lower end of the balancing weight 170, fixation is performed.

In this manner, the first wire 162 and the second wire 164 are fastened and fixed to upper and lower ends of the sliding frame 123 and upper and lower ends of the balancing weight 170 while being wound on the first wheel 151 and the second wheel 152, respectively, through the wire fixing screws, and form a wire structure having a closed loop shape without a disconnected part.

As described above, both ends of the first wire 162 and the second wire 164 are detachably combined with the fixing bracket 124 of the sliding frame 123 and the balancing weight 170 using the wire fixing screws. Therefore, since the wire fixing screws fixed to both ends of the first and second wires 162 and 164 can be easily separated from and recombined with the fixing bracket 124 of the sliding frame 123 or the balancing weight 170 as necessary, it is possible to easily replace or repair a component when an internal component is damaged.

In addition, since the two wires 162 and 164 have a closed loop shape between the first wheel 151 and the second wheel 152 and has a tightly connected structure, even when a mode of the X-ray detecting device is changed from a standing imaging mode in an upright state to a table imaging mode in a horizontal state, it is possible to prevent the wires 162 and 164 wound on the first wheel 151 and the second wheel 152 inside the support frame 130 from being released and separated from the wheel. Therefore, it is possible to prevent damage or safety problems of devices that can be caused when the wires 162 and 164 wound on the wheels 151 and 152 are released and the balancing weight 170 is separated from its own position.

Figure 7:
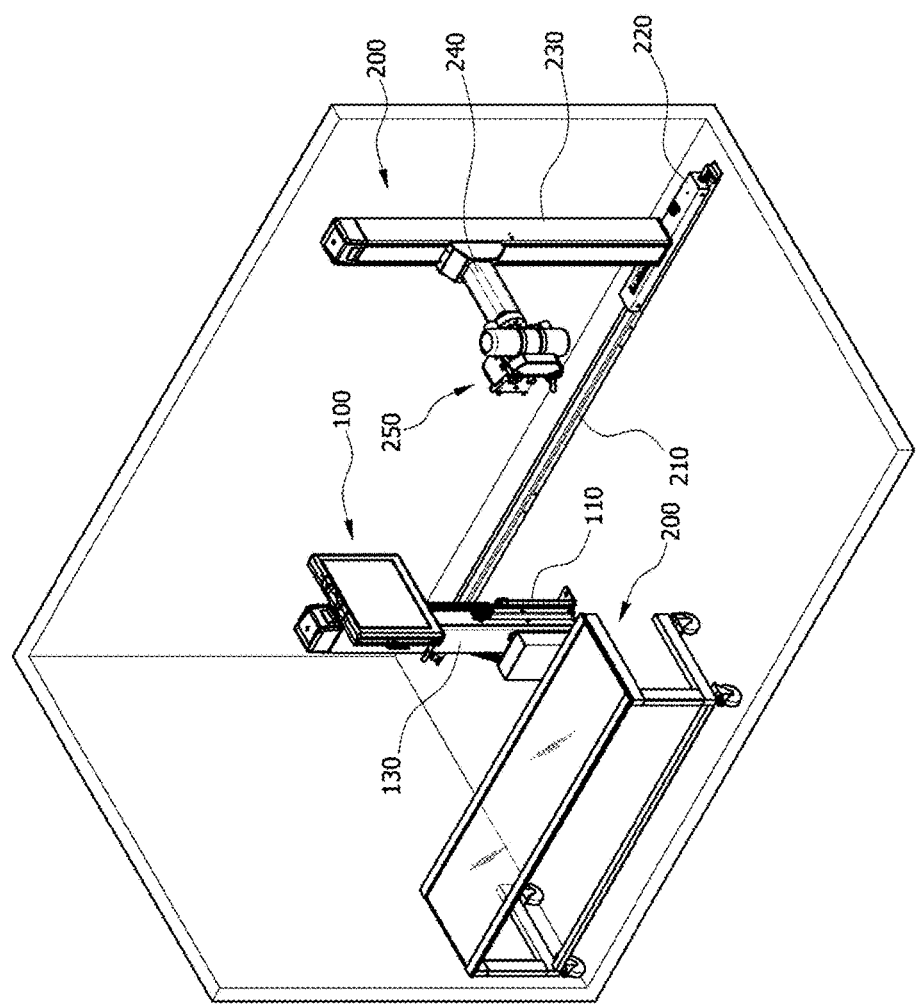
FIG. 7 is a disposition diagram illustrating a state in which the X-ray imaging apparatus is disposed when imaging is performed in a standing mode using the X-ray imaging apparatus according to the present invention.

Meanwhile, FIG. 7 illustrates a state in which an entire X-ray imaging apparatus including the X-ray generating device and the X-ray detecting device is disposed when X-ray imaging is performed in the standing mode using the X-ray detecting device 100 of the present invention.

As illustrated in FIG. 7, when X-ray imaging is performed in the standing mode, while the actuator is driven and the support frame 130 of the X-ray detecting device 100 remains in an upright state (perpendicular to the bottom surface), imaging is performed. In this case, while the operator who performs the X-ray imaging task manually or automatically manipulates the X-ray detector 120 such that the X-ray detector 120 is positioned at an appropriate imaging target area of the patient and a height is adjusted, X-rays are emitted to the X-ray detecting device 100 through an X-ray generating device 200 disposed at a rear side and then imaging is performed.

Here, a configuration of the X-ray generating device 200 configured to emit X-rays to the X-ray detecting device 100 of the present invention includes a transfer body 220 that is slidably installed in a front and rear direction (a left and right direction in the drawing) along a rail 210 fixed to the bottom surface, a vertical frame 230 that vertically stands on and is combined with the transfer body 220, an arm 240 that is disposed perpendicularly to the vertical frame 230 and vertically transfers in a lengthwise direction of the vertical frame 230, and an X-ray generator 250 pivotally mounted on an end of the arm 240. The X-ray generating device 200 configured in this manner is used, the X-ray generator 250 is moved in a front and rear direction or a vertical direction, a position thereof is adjusted to be placed at an appropriate imaging position, and then X-rays are emitted to the X-ray detector 120. Therefore, it is possible to easily image each area of a body such as a chest or a head of the patient.

Figure 8:
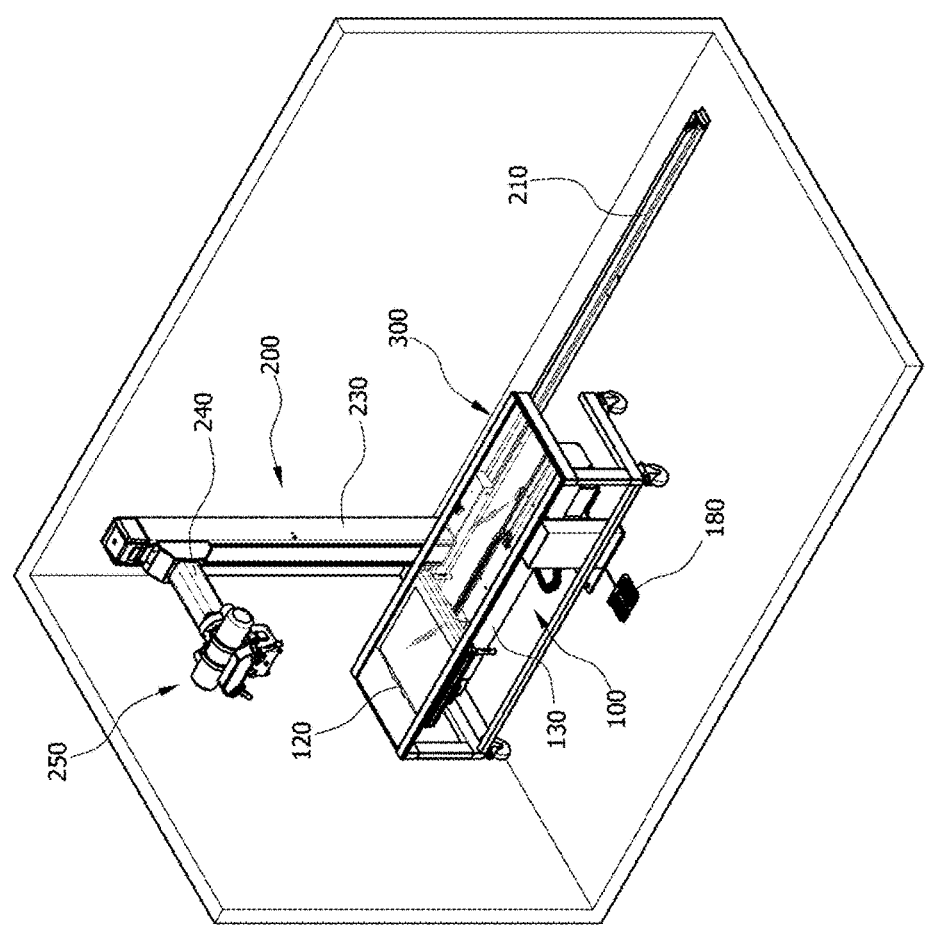
FIG. 8 is a disposition diagram illustrating a state in which the X-ray imaging apparatus is disposed when imaging is performed in a table mode using the X-ray imaging apparatus of the present invention.

Meanwhile, FIG. 8 illustrates a state in which an entire X-ray imaging apparatus is disposed when X-ray imaging is performed in a table mode using the X-ray detecting device 100 of the present invention described above.

As illustrated in FIG. 8, in table mode imaging in which X-ray imaging is performed while the patient is lying on the table, while the actuator is driven and the support frame 130 of the X-ray detecting device 100 is bent at 90 degrees to be parallel to the bottom surface and remains in a horizontal state, imaging is performed. In this state, while a table 300 whose one side surface is open is moved to the X-ray detecting device 100 and the X-ray detecting device 100 is disposed to be positioned in the table 300, a position adjusting task of the X-ray generator 250 is performed such that the X-ray generator 250 is positioned above a side opposite to the X-ray detector 120, and then the X-ray imaging task can be performed while the patient is lying on the table 300.

Figure 9:
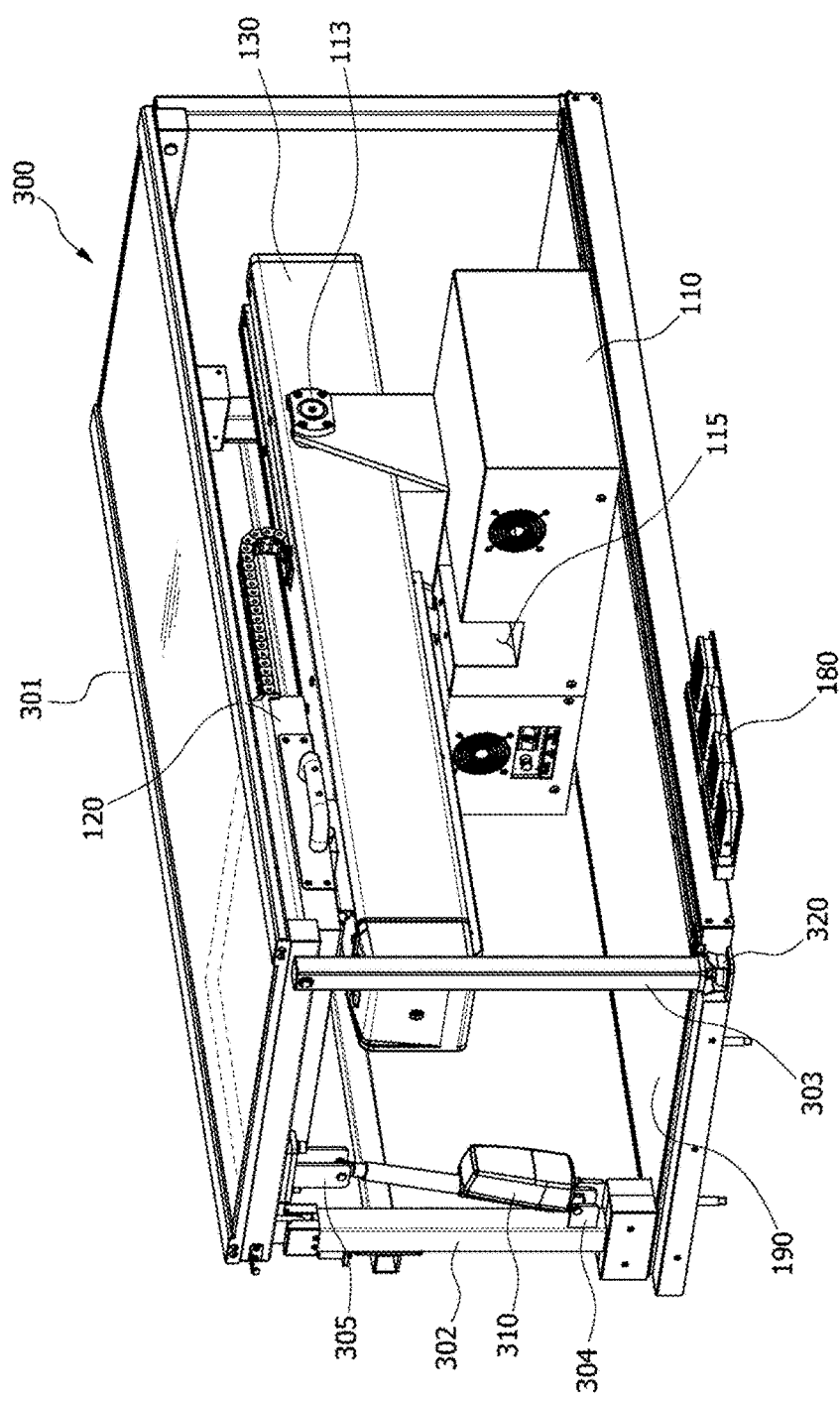
FIG. 9 is a perspective view of an X-ray imaging apparatus according to a second embodiment of the present invention.
Figure 10:
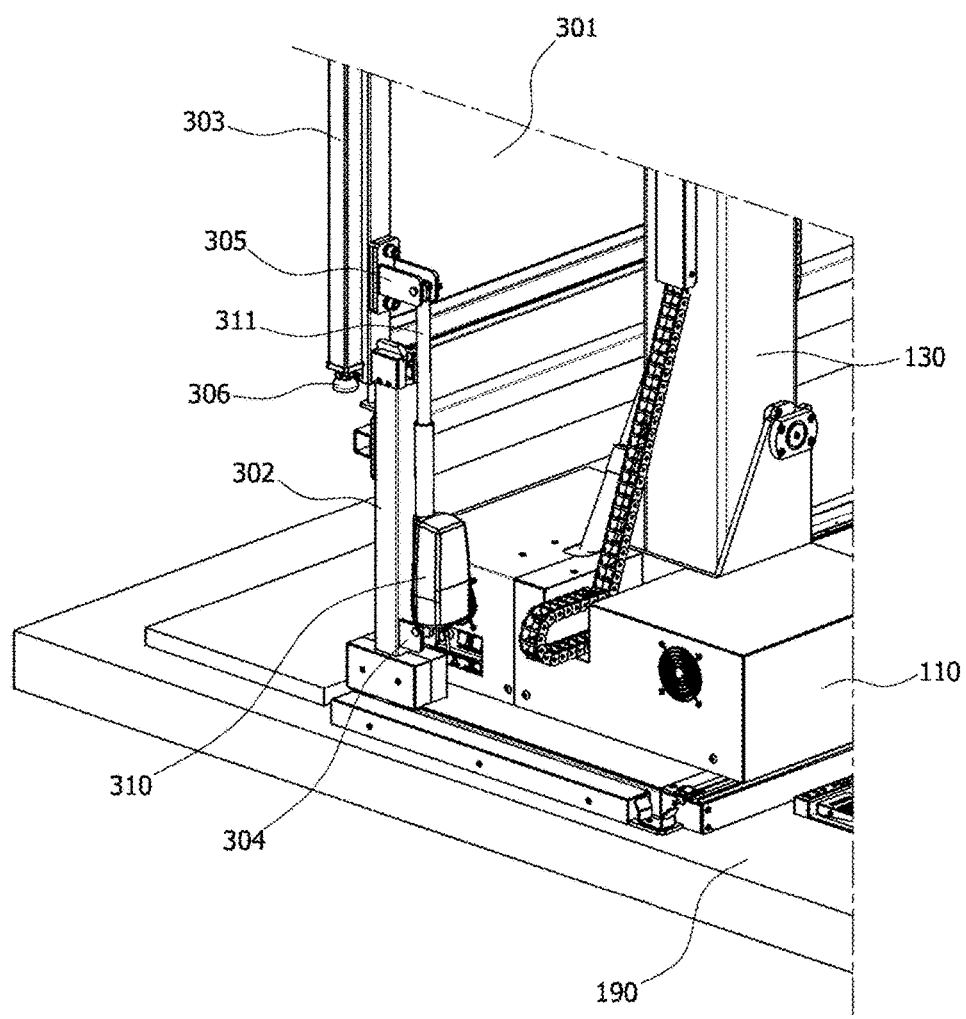
FIG. 10 is a detail view illustrating a detailed part of a table tilting device illustrated in FIG. 9.
Figure 11:
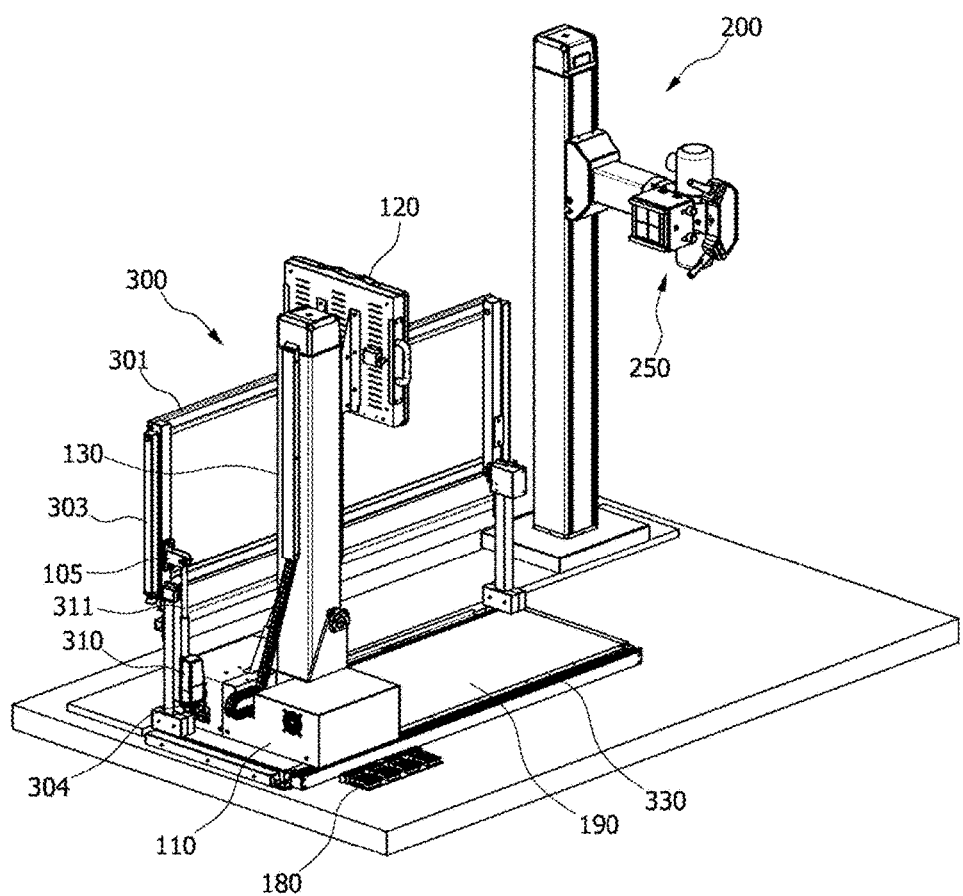
FIG. 11 is a usage state diagram illustrating a state in which a table is completely tilted up in order to perform imaging in a standing mode in the X-ray imaging apparatus of FIG. 9.
Figure 12:
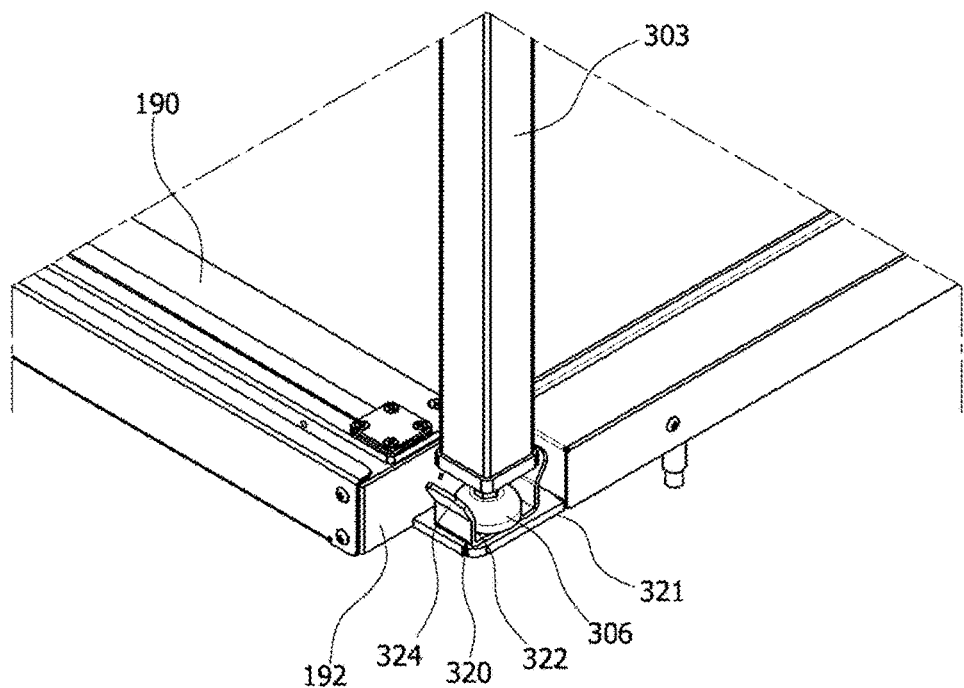
FIG. 12 is a partial perspective view illustrating a state in which a lower end of a rotating leg portion of a table is parked in a parking device provided in a bottom portion of the present invention.
Figure 13:
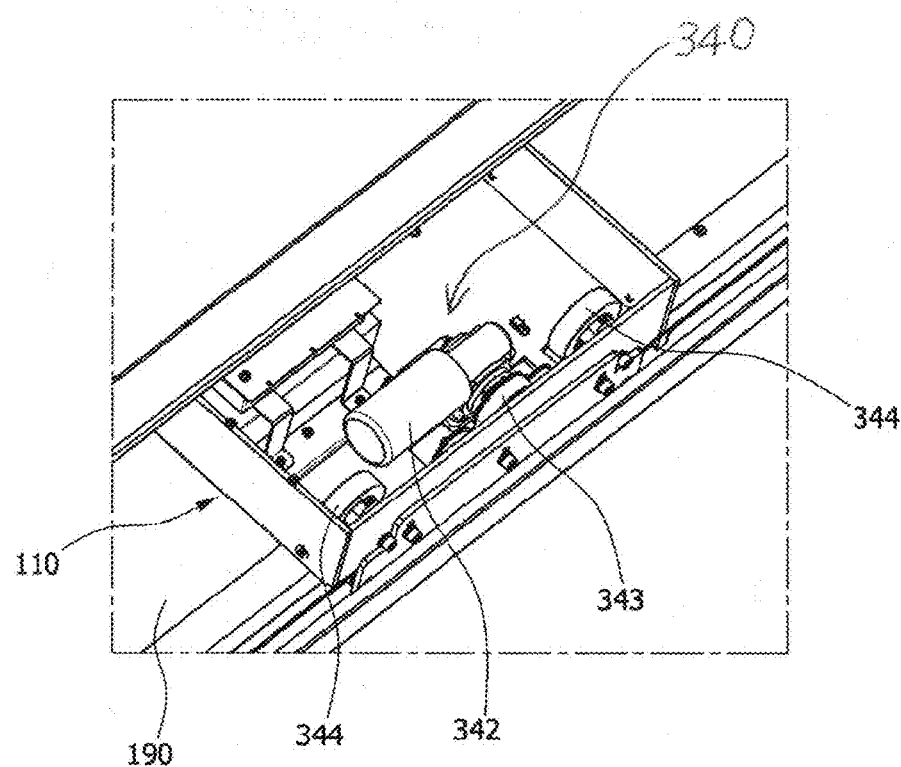
FIG. 13 is a partial perspective view illustrating a state in which a driving unit for a sliding linear movement is installed inside a base frame of the present invention.

Meanwhile, FIG. 9 is a perspective view of an X-ray imaging apparatus according to a second embodiment of the present invention. FIG. 10 is a detail view illustrating a detailed part of a table tilting device of FIG. 9. Also, FIG. 11 is a usage state diagram illustrating a state in which a table is completely tilted up in order to perform imaging in a standing mode in the X-ray imaging apparatus of FIG. 9. FIG. 12 is a partial perspective view illustrating a state in which a lower end of a rotating leg portion of a table is parked in a parking device provided in a bottom portion. FIG. 13 is a partial perspective view illustrating a state in which a driving unit for a sliding linear movement is installed in a base frame.

Unlike the X-ray imaging apparatus of the first embodiment described above, the X-ray imaging apparatus according to the second embodiment of the present invention has a configuration in which the X-ray detecting device 100 and the table 300 form one set above a bottom portion 190 in an assembling manner. Even in a narrow space, that is, a very small installation space, it is possible to easily perform imaging by variously changing a mode to the standing or table mode through the X-ray detecting device 100 of the present invention.

As illustrated in FIGS. 9 to 13, the X-ray imaging apparatus according to the second embodiment of the present invention includes the base frame 110 installed to be slidably linearly movable on the bottom portion 190, the support frame 130 pivotally combined with one side of the base frame 110 and having one side at which the X-ray detector 120 configured to detect X-rays emitted from an X-ray generating device is slidably installed, the actuator 140 including one end that is pivotally fixed to the base frame 110 and the other end that is pivotally fixed to the support frame 130, and enabling the support frame 130 to be pivoted in a predetermined angle range, a driving unit configured to drive such that the base frame 110 slidably linearly moves on the bottom portion 190, the table 300 installed above the bottom portion 190 in a tiltable manner, a tilting unit configured to tilt the table 300, and a control unit configured to control the actuator 140, the driving unit and the tilting unit.

Here, basic configurations and functions of the base frame 110, the support frame 130 with which the X-ray detector 120 is slidably combined, and the actuator 140 configured to pivot the support frame 130 in a certain angle range of the X-ray detecting device 100 according to the second embodiment of the present invention are the same as those in the first embodiment described above. Therefore, only configurations of the second embodiment different from the first embodiment described above will be described below in detail.

The X-ray imaging apparatus according to the second embodiment of the present invention has a configuration in which the X-ray detecting device 100 that is horizontally movable and the table 300 that is tiltable form one set in an assembling manner above the bottom portion 190 forming a certain rectangular space.

Specifically, the base frame 110 in which the support frame 130 provided with the X-ray detector 120 is supported to be rotatable has a rectangular box shape, and is installed to be slidably linearly movable in a front and rear direction along an upper surface of the bottom portion 190.

In a center of an upper end of the base frame 110, a groove 115 that has a certain width and is recessed downward such that a lower end of the support frame 130 is not interfered with and is able to freely pass when the support frame 130 is pivoted is formed.

Also, the actuator (not illustrated) having the same shape as in the first embodiment described above is provided inside the base frame 110 such that the support frame 130 provided with the X-ray detector 120 can be pivoted in a predetermined angle range.

Also, as illustrated in FIG. 13, in the base frame 110, a driving unit 340 configured to drive such that the base frame 110 slidably linearly reciprocates along an upper surface of the bottom portion 190 is installed.

The driving unit 340 includes a driving motor 342 installed inside the base frame 110, a plurality of casters 344 that are rotatably installed at a lower end of the base frame 110 and move along the upper surface of the bottom portion 190 in a rolling manner, and a power transmission device 343 connecting the driving motor 342 and the caster 344 and configured to transmit power of the driving motor 342 to the caster 344. Also, the driving unit includes a guide unit configured to guide such that the caster 344 installed at the lower end of the base frame 110 can linearly reciprocally move along a determined linear trajectory.

The driving motor 342 is connected to a control unit 180 positioned at the bottom portion 190, is driven forward or backward through the control unit 180, rotates the caster 344, and provides a driving force such that the base frame 110 is slidably moved to the upper surface of the bottom portion 190.

The control unit 180 configured to control the driving motor 342 controls the actuator 140 and the driving unit such that a sliding linear movement of the base frame 110 and a rotational movement of the support frame 130 with respect to the base frame 110 can be simultaneously performed.

As the control unit 180, a foot switch having a shape as illustrated in FIG. 9 may be applied in order for the user to easily perform manipulation using his or her foot. Such a foot switch can be configured such that tilting up and down of the table 300, sliding in a front and rear direction of the base frame 110, and a forward or backward rotational movement of the support frame 130 can be controlled separately or simultaneously.

The power transmission device 343 is a device configured to reduce the number of revolutions of the driving motor 342 at a certain ratio and transmit power to the caster 344, and may be configured as a combination of a plurality of gears or a combination of a pulley, a belt, a chain and the like.

The guide unit is a device configured to reciprocate the base frame 110 along a determined linear trajectory above the bottom portion 190. The guide unit may be configured such that, for example, a guide piece protruding downward from a side surface of the base frame 110 is formed, a linear groove into which the guide piece is inserted is formed on the bottom portion 190, and when the base frame 110 slidably moves, the base frame 110 reciprocates along a determined linear trajectory through the guide piece and the linear groove.

Also, when it is configured such that the caster 344 of the lower end of the base frame 110 is inserted into the linear groove formed on the bottom portion 190 and then moves along the linear groove in a rolling manner, the base frame 110 may move along a determined linear trajectory above the bottom portion 190.

Meanwhile, the table 300 includes a rectangular upper plate 301 on which the patient can lie on, and four leg portions 302 and 303 provided at lower ends of four corners of the rectangular upper plate 301.

Among the four leg portions 302 and 303 provided in the table 300, the two leg portions 302 at one side are fixed to the bottom portion 190, and the two leg portions 303 at the other side are freely detachable from the bottom portion 190.

That is, the pair of fixed leg portions 302 provided at a long side part of the table 300 have lower ends that are fixed to the bottom portion 190 and upper ends that are rotatably combined with a part of the upper plate 301 by a hinge. In addition, the pair of rotating leg portions 303 provided at an opposite long side part of the upper plate 301 facing the fixed leg portion 302 have upper ends that are rotatably combined with a part of the upper plate 301 by a hinge and lower ends that are mounted on the bottom portion 190.

Meanwhile, a table tilting unit is connected to the control unit 180, and enables the table 300 to be tilted up or tilted down according to a control signal applied from the control unit 180.

Such a tilting unit 309 includes a first bracket 304 combined with the fixed leg portion 302, a second bracket 305 combined with the upper plate 301, and a cylinder 310 that is provided between the first bracket 304 and the second bracket 305, expands and contracts a rod 311 provided therein, and thus drives the upper plate 301 to be tilted up and down.

The first bracket 304 has a structure protruding from one side surface of the fixed leg portion 302 for combination. The second bracket 305 has a structure protruding from a lower end of a side surface of the upper plate 301 for combination. Also, a lower end of the cylinder 310 is rotatably combined with the first bracket 304 by a hinge, and the rod 311 at the upper end of the cylinder 310 is rotatably combined with a part of the second bracket 305 by a hinge.

The cylinder 310 may include, for example, a pneumatic cylinder that is operated using a pneumatic pressure, a hydraulic cylinder that is operated using a hydraulic pressure, or an electric cylinder configured to rotate a motor inside the cylinder forward or backward when power is applied and reciprocate the rod. In the present embodiment, the electric cylinder that is operated using electricity is used and thus a tilting operation of the table may be performed more precisely.

One tilting unit may be installed at either of the pair of fixed leg portions 302 of the table 300 as in the present embodiment, or the tilting unit may be installed at both of the fixed leg portion 302.

Meanwhile, FIG. 12 illustrates a state in which a lower end of the rotating leg portion 303 of the table 300 is parked in the parking device provided in the bottom portion 190 in the table mode in which the upper plate 301 is tilted down.

As illustrated in FIG. 12, in a part of the bottom portion 190 on which the lower end of the rotating leg portion 303 of the table 300 is mounted, a parking device 320 configured to park the rotating leg portion 303 to be mounted at a determined position is provided.

The parking device 320 is installed into a groove 192 formed at both corner parts of the bottom portion 190. The parking device 320 includes a leg pedestal portion 306 made of a shock-absorbing material attached to the lower end of the rotating leg portion 303, a U-shaped mounting unit 322 on which the leg pedestal portion 306 is inserted and mounted, and a leading unit 324 configured to lead the leg pedestal portion 306 to be inserted into the mounting unit 322.

The leg pedestal portion 306 fixed to the lower end of the rotating leg portion 303 is made of a shock-absorbing material such as a rubber or silicone material in order to relieve shock when the table 300 is tilted down and the rotating leg portion 303 moves down and comes in contact with the ground.

The mounting unit 322 has a U-shaped plate whose upper part is open and both facing side surfaces of one side are open. At an upper end of the mounting unit 322, the leading unit 324 that is obliquely bent outward, and when the rotating leg portion 303 moves down, induces the leg pedestal portion 306 into the mounting unit 322 to be easily inserted and mounted is formed.

Also, the mounting unit 322 is firmly attached and fixed to an upper surface of a fixing member 321 made of the shock-absorbing material as in the leg pedestal portion 306.

Figure 14:
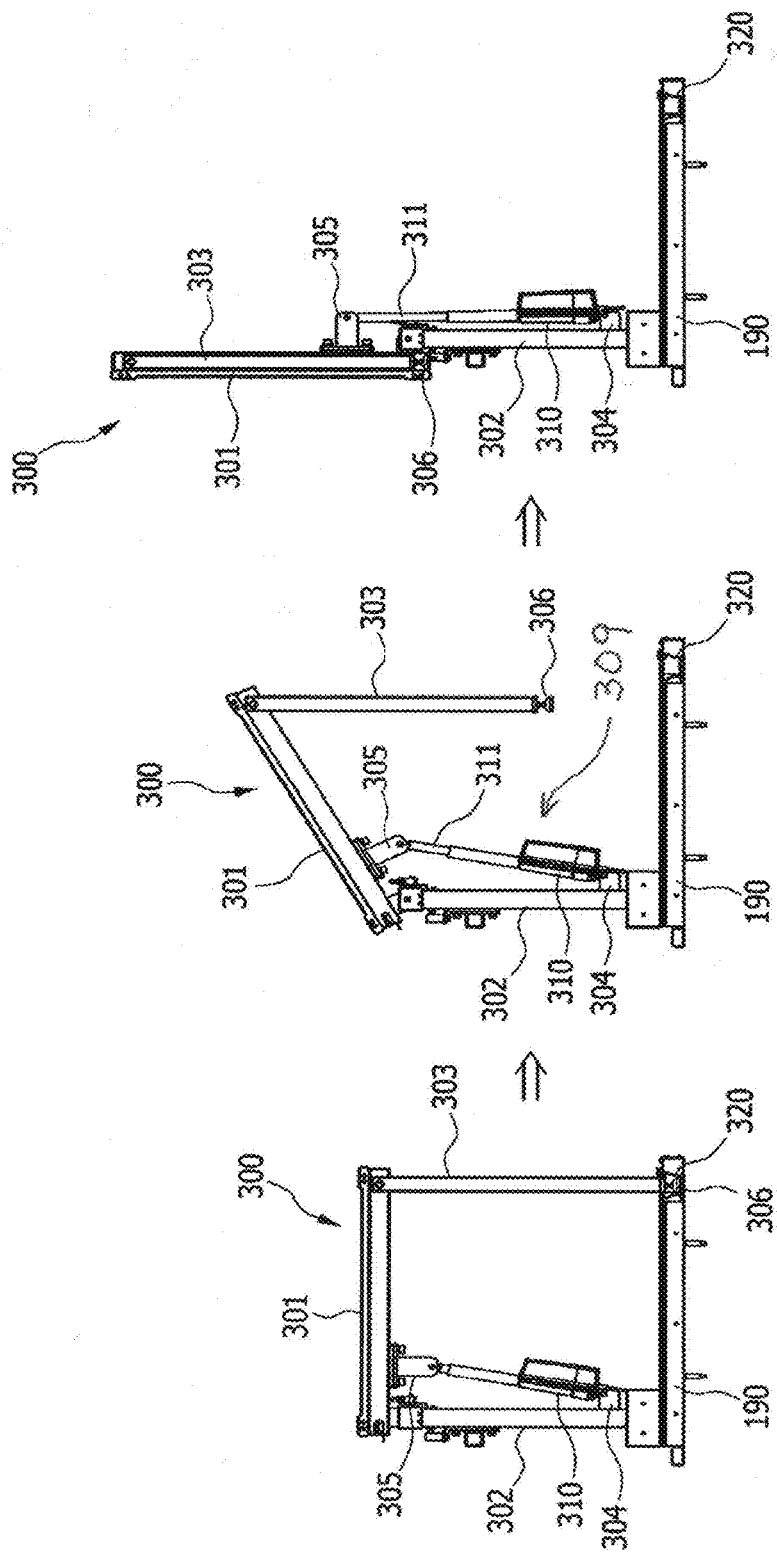
FIG. 14 is an operation state diagram sequentially illustrating a process in which a table according to the present invention is tilted up by a tilting unit.

FIG. 14 is an operation state diagram sequentially illustrating a process in which the table 300 is tilted up by the tilting unit in the X-ray imaging apparatus according to the second embodiment of the present invention.

FIG. 14A illustrates a state of the table 300 when the X-ray imaging; apparatus of the present invention performs imaging in the table mode. In the table mode, the leg pedestal portion 306 of the lower end of the rotating leg portion 303 of the table 300 is mounted into the parking device 320 and remains in a fixed state without an unbalanced sliding motion in a horizontal direction.

In this state, when a mode of the table 300 is changed to the standing mode, if a control signal is applied to the cylinder 310 through the control unit 180, the rod 311 inside the cylinder 310 is withdrawn, and the upper plate 301 hinged to the fixed leg portion 302 is moved up in a rotating manner as illustrated in FIG. 14B. In this process, the leg pedestal portion 306 provided at the lower end of the rotating leg portion 303 is separated from the parking device 320.

Then, in a state in which the rod 311 of the cylinder 310 is completely withdrawn and the upper plate 301 is lifted up to the top, as illustrated in FIG. 14C, the upper plate 301 of the table 300 is in parallel with the fixed leg portion 302. After the table 300 is completely tilted up in this manner, the control unit 180, that is, the foot switch, is manipulated, the support frame 130 of the X-ray detecting device stands upright with respect to the base frame 110, and thus an imaging task can be performed in the standing mode.

Meanwhile, when a mode of the table 300 is changed to the table mode again, a control signal in a reverse direction is applied to the cylinder 310 through the control unit 180, the upper plate 301 is tilted down through a contraction operation of the rod 311 of the cylinder and a state is restored to the initial (a).

Figure 15:
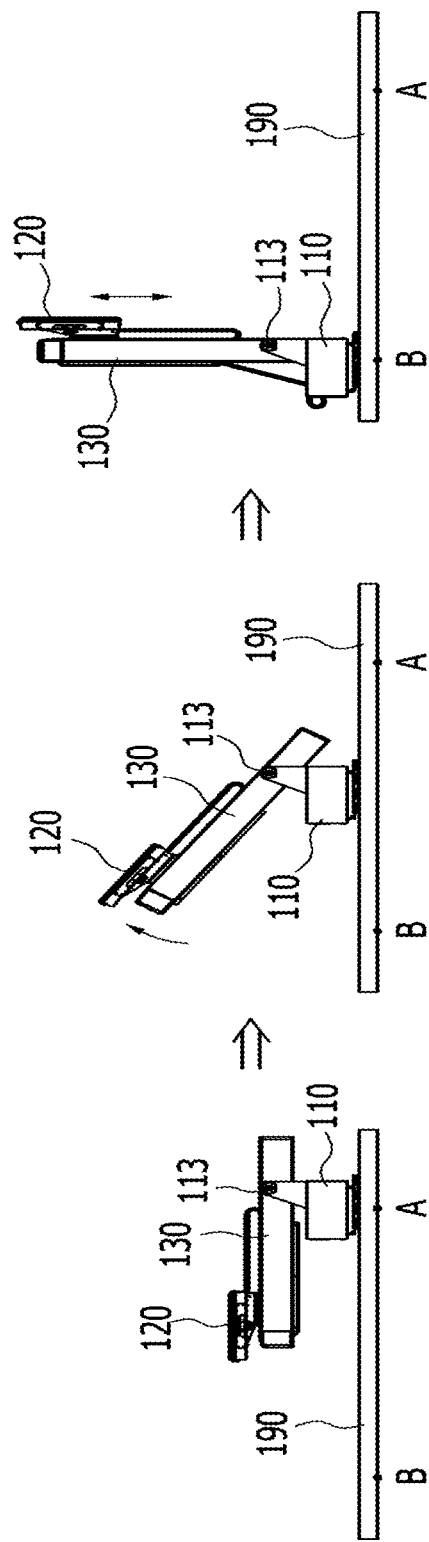
FIG. 15 is an operation state diagram illustrating a state in which a sliding linear movement of a base frame and a rotational movement of a support frame according to the present invention are simultaneously performed.

FIG. 15 is an operation state diagram sequentially illustrating a process in which, while the table 300 is tilted up in the standing imaging mode as in FIG. 14C, the base frame 110 slidably moves in a horizontal direction and simultaneously the support frame 130 of the X-ray detecting device stands upright with respect to the base frame 110.

After the table 300 is tilted up and a mode is switched to the standing mode, if a control signal is applied to the driving motor provided inside the base frame 110 through the control unit 180, the base frame 110 slidably moves from a point "A," which is an initial position of the bottom portion 190, to a point "B" as illustrated in FIG. 15A. In this case, according to driving of the actuator inside the base frame 110 as illustrated in FIG. 15B in linkage with a sliding movement of the base frame 110, the support frame 130 is gradually raised from the base frame 110, the support frame 130 is completely upright with respect to the base frame 110 at the point "B" at which the sliding movement of the base frame 110 ends, and thus the imaging task can be performed in the standing imaging mode.

As described above, according to the X-ray imaging apparatus of the present invention, the actuator 140 installed in the X-ray detecting device 100 is driven, an imaging orientation mode of the X-ray detecting device 100 is changed to various modes such as the standing mode or the table mode, and thus the X-ray imaging task can be performed quickly and conveniently. In addition, imaging can be performed using one X-ray detecting device 100 by easily changing a mode to various imaging modes including the standing mode and the table mode, unlike the related art. Therefore, since there is no need to separately provide a dedicated imaging apparatus for performing imaging in the standing mode or the table mode, it is possible to reduce an installation cost, and since a separate dedicated installation space for each imaging mode is unnecessary, it is possible to maximize a space utilization.

In addition, according to the X-ray detecting device 100 of the present invention, a wire connection structure having a closed loop shape in which the first wheel 151 and the second wheel 152 are rotatably fixed to the inner upper and lower ends of the support frame 130, and the wire 160 is wound on and connects the first wheel 151 and the second wheel 152 is formed. Therefore, when a mode of the X-ray detecting device 100 is switched from the standing imaging mode to the table imaging mode or switched from the table imaging mode to the standing imaging mode, it is possible to prevent the wire 160 wound between the two wheels 151 and 152 from being released and separated. In addition, it is possible to prevent internal component damage and safety problems caused when the wire 160 is separated from the wheels 151 and 152 and thus the balancing weight 170 is separated.

Also, the X-ray detecting device 100 is installed to be horizontally movable in a front and rear direction and simultaneously the table 300 is installed to be tiltable in a vertical direction. Therefore, when imaging is performed in the standing mode, the imaging task can be performed while the table 300 is tilted and then the X-ray detecting device 100 is horizontally moved in one direction and is in an upright state. When imaging is performed in the table mode, the upright X-ray detecting device 100 is moved in an opposite direction again and is placed in a horizontal state, the table 300 is restored to an original state again, and the imaging task can be easily performed in the table mode. Therefore, even in a narrow space, that is, a limited space, it is possible to easily perform the X-ray imaging task by freely changing a mode to the standing mode or the table mode using the X-ray imaging apparatus of the present invention. It is possible to suppress an increase of additional costs necessary for ensuring an installation space according to separate installation of the X-ray detecting device and the table in different spaces.

While embodiments of the present invention have been described above, the scope of the present invention is not limited to the embodiments. Those skilled in the art can appropriately make changes within the scope defined by the appended claims of the present invention.

The invention claimed is:

1. An X-ray imaging apparatus capable of performing imaging in various imaging modes, comprising:
   a base frame;
   a support frame pivotally combined with one side of the base frame and having one side at which an X-ray detector configured to detect X-rays emitted from an X-ray generating device is slidably installed;
   an actuator including one end that is pivotally fixed to the base frame and the other end that is pivotally fixed to the support frame, and enabling the support frame to be pivoted in a predetermined angle range;
   a first wheel rotatably fixed to one inner end of the support frame;
   a second wheel rotatably fixed to the other inner end of the support frame facing the first wheel;
   one or more wires connected to the first wheel and the second wheel to form a loop; and
   a balancing weight configured to maintain a balance with the X-ray detector.

2. The X-ray imaging apparatus of claim 1, wherein the one or more wires comprise:
   a first wire including one end that is fixed to the X-ray detector and the other end that is fixed to the balancing weight while being wound on the first wheel; and
   a second wire including one end that is fixed to the X-ray detector and the other end that is fixed to the balancing weight while being wound on the second wheel.

3. The X-ray imaging apparatus of claim 1, further comprising
   a driving motor installed at the support frame and configured to transmit rotary power to either the first wheel or the second wheel; and
   a manipulation switch configured to manipulate the driving motor to be rotatably driven forward or backward.

4. The X-ray imaging apparatus of claim 2,
   wherein the X-ray detector includes
   a detector body having a plate shape; and
   a sliding frame that is combined with a rear side of the body and configured to slidably move in a lengthwise direction of the support frame,
   wherein ends of one side of the first wire and the second wire are detachably connected through a fixing bracket fixed to the sliding frame.

5. The X-ray imaging apparatus of claim 4,
   wherein both ends of the first wire and both ends of the second wire are detachably combined with the fixing bracket of the sliding frame and the balancing weight through wire fixing screws.

6. An X-ray imaging apparatus capable of performing imaging in various imaging modes, comprising:
   a base frame installed to be slidably linearly movable on a bottom portion;
   a support frame pivotally combined with one side of the base frame and having one side at which an X-ray detector configured to detect X-rays emitted from an X-ray generating device is slidably installed;
   an actuator including one end that is pivotally fixed to the base frame and the other end that is pivotally fixed to the support frame, and enabling the support frame to be pivoted in a predetermined angle range;
   a driving unit configured to drive such that the base frame slidably linearly moves on the bottom portion;
   a table installed above the bottom portion in a tiltable manner;
   a tilting unit configured to tilt the table; and
   a control unit configured to control the actuator, the driving unit, and the tilting unit.

7. The X-ray imaging apparatus of claim 6,
   wherein the control unit controls the driving unit and the actuator such that a sliding linear movement of the base frame and a rotational movement of the support frame with respect to the base frame are able to be performed simultaneously.

8. The X-ray imaging apparatus of claim 6,
   wherein the control unit is a foot switch that is attached to the bottom portion and is manipulated by a foot.

9. The X-ray imaging apparatus of claim 6,
   wherein the table includes
   an upper plate;
   a pair of fixed leg portions whose lower end is fixed to the bottom portion and whose upper end is rotatably combined with the upper plate by a hinge; and
   a pair of rotating leg portions that are positioned at a side opposite to the upper plate facing the fixed leg portion and have an upper end that is rotatably combined with the upper plate by a hinge and a lower end that is mounted on the bottom portion.

10. The X-ray imaging apparatus of claim 9,
    wherein a parking device configured to park the rotating leg portion to be mounted at a normal position is installed in a part of the bottom portion on which the rotating leg portion is mounted.

11. The X-ray imaging apparatus of claim 10,
    wherein the parking device is installed into a groove formed at both corner parts of the bottom portion.

12. The X-ray imaging apparatus of claim 10,
    wherein the parking device includes
    a leg pedestal portion made of a shock-absorbing material attached to a lower end of the rotating leg portion;
    a U-shaped mounting unit on which the leg pedestal portion is inserted and mounted; and
    a leading unit configured to lead the leg pedestal portion to be inserted into the mounting unit.

13. The X-ray imaging apparatus of claim 9,
    wherein the tilting unit includes
    a first bracket combined with a fixed leg portion;
    a second bracket combined with an upper plate; and
    a cylinder that includes a lower end combined with the first bracket by a hinge and an upper end combined with the second bracket by a hinge, and tilts up and down the upper plate.

14. The X-ray imaging apparatus of claim 13
wherein the cylinder is an electric cylinder that rotates a motor inside the cylinder forward or backward when power is applied and reciprocates a rod.

15. The X-ray imaging apparatus of claim 9,
wherein the tilting unit is installed at at least one of a pair of fixed leg portions.

16. The X-ray imaging apparatus of claim 8,
wherein the driving unit includes
a driving motor installed inside the base frame;
a plurality of casters that are rotatably installed at a lower end of the base frame and move along an upper surface of the bottom portion in a rolling manner;
a power transmission device connecting the driving motor and the caster and configured to transmit power of the driving motor to the caster; and
a guide unit configured to guide the caster to be moved along a determined linear trajectory.

* * * * *